United States Patent [19]
Rosengaus et al.

[11] Patent Number: 6,020,957
[45] Date of Patent: Feb. 1, 2000

[54] SYSTEM AND METHOD FOR INSPECTING SEMICONDUCTOR WAFERS

[75] Inventors: Eliezer Rosengaus, Palo Alto; Steven R. Lange, Alamo, both of Calif.

[73] Assignee: KLA-Tencor Corporation, San Jose, Calif.

[21] Appl. No.: 09/070,437

[22] Filed: Apr. 30, 1998

[51] Int. Cl.[7] .................................................. G01N 21/89
[52] U.S. Cl. ................................................................ 356/237.4
[58] Field of Search ............................. 356/237.3, 237.4, 356/237.5, 239.7, 239.8

[56] References Cited

U.S. PATENT DOCUMENTS

| | | | |
|---|---|---|---|
| 4,877,326 | 10/1989 | Chadwick et al. | 356/394 |
| 5,177,559 | 1/1993 | Batchelder et al. | 356/237 |
| 5,274,434 | 12/1993 | Morioka et al. | 356/237.4 |
| 5,463,459 | 10/1995 | Morioka et al. | 356/237 |
| 5,644,393 | 7/1997 | Nakamura et al. | 356/237.3 |

*Primary Examiner*—Richard A. Rosenberger
*Attorney, Agent, or Firm*—Beyer & Weaver, LLP

[57] ABSTRACT

A method for inspecting semiconductor wafers is provided in which a plurality of independent, low-cost, optical-inspection subsystems are packaged and integrated to simultaneously perform parallel inspections of portions of the wafer, the wafer location relative to the inspection being controlled so that the entire wafer is imaged by the system of optical subsystems in a raster-scan mode. A monochromatic coherent-light source illuminates the wafer surface. A darkfield-optical system collects scattered light and filters patterns produced by valid periodic wafer structures using Fourier filtering. The filtered light is processed by general purpose digital-signal processors. Image subtraction methods are used to detect wafer defects, which are reported to a main computer to aid in statistical process control, particularly for manufacturing equipment.

38 Claims, 14 Drawing Sheets

1

SYSTEM AND METHOD FOR INSPECTING SEMICONDUCTOR WAFERS

BACKGROUND OF THE INVENTION

This application relates to an apparatus and method for optical inspection of semiconductor wafers. In particular, the apparatus and method of the present invention provide high-throughput inspection of wafers using a plurality of independent good sensitivity, low-cost inspection devices whose packaging and form factor allow operation in parallel. The present invention may be applied to brightfield and/or darkfield inspection systems.

Optical inspection of semiconductor wafers has become a standard step in the production of semiconductors. Wafers are illuminated with light emanating from a controlled illuminator, and an image of the surface is constructed based on the portion of the light reflected or otherwise directed to a light sensor. The image is processed to isolate defects from valid structures.

The sensitivity of optical inspection systems to small sized defects on a patterned wafer surface is determined by the ability of the system to discriminate between a defect signal and a valid structure signal. In brightfield inspection systems, sensors register light reflected from the wafer surface typically achieving pixel-to-defect ratio sensitivities of 1:1 or 2:1. In darkfield systems, sensors register the scattered and diffracted light, the light which deviates from a perfect reflection. In contrast to brightfield systems, darkfield systems can easily achieve a 10:1 or 20:1 pixel-to-defect ratio for certain common defects.

Optical inspection systems are either imaging or non-imaging. In imaging systems, a lens captures light reflected from an area on the wafer surface and preserves the spatial information encoded in that light (e.g., a spatial distribution of light intensity). Sensors are typically arrays of light-sensitive detectors such as charge-coupled device (CCD) "cameras" or, more recently, CMOS photodiode or photogate cameras.

In contrast, in non-imaging systems the light from the illuminator is concentrated on a small area (ideally a very small point) on the wafer's surface. A sensor—for example a photomultiplier tube, photodiode, or avalanche photodiode—detects scattered, or diffracted light, and produces a signal proportional to the integrated light intensity.

Others have concentrated on attempting to maximize sensitivity in order to detect the defects of the smallest size. Consequently, expensive special-purpose optical, mechanical, electronic, and computer processing systems have been employed in state-of-the-art tools. For example, these systems may allow adjustments in magnification levels, illumination angles, and polarization, each of which further increases system complexity and cost. The components in each sensing subsystem of the present invention are limited to performing only one type of inspection, further reducing cost by eliminating complexity. The present invention's individual subsystems emphasize compactness and low-cost over sensitivity, providing a system with medium sensitivity and high levels of throughput. Increasing the throughput of such systems stresses the design of these components and further increases the cost.

Some applications do not require the high level of sensitivity produced by such systems. In equipment monitoring, for example, a statistical process may be used to indicate whether the equipment used during a manufacturing step is functioning correctly. The sensitivity, in this case, need only be high enough to detect when the manufacturing equipment is causing a statistically significant excess number of defects (excursion). Since this type of application is most useful if repeated often (after every manufacturing step, for example), fast examination speed is important to keep up with the manufacturing process.

What is needed therefore is a fast and relatively inexpensive tool for monitoring the condition of wafers at various points in the integrated circuit manufacturing process.

SUMMARY OF THE INVENTION

The present invention addresses the problem by providing a high-throughput inspection system at low cost, particularly for equipment monitoring applications. A single low-cost unit can be provided using "consumer grade" devices for illumination, imaging, image sensing, and image-processing which can measure a part of the wafer by itself with acceptable sensitivity, and with very high speed. A system can be provided utilizing a plurality of single units which can be scanned over the wafer together to complete the measurement. Miniaturization provides a form factor such that a plurality of the units can be packaged together. Each unit operates independently scanning a swath across the wafer parallel to adjacent units. Together, the stacked parallel units scan the wafer. The cost savings using the consumer grade components, even with a plurality of units, is large compared to the system of others while providing comparable sensitivity and faster throughput.

The components in each sensing subsystem of the present invention generally perform one type of inspection (e.g., imaging scattered radiation from a semiconductor substrate), further reducing cost by eliminating complexity. The present invention's individual subsystems emphasize compactness and low-cost over versatility, providing a system with good sensitivity and high levels of throughput.

In one aspect, the invention provides a multi-stage integrated circuit manufacturing system employing a modular optical inspection system for inspecting a semiconductor wafer. The manufacturing system may be characterized as including the following features: (a) a plurality of interrelated integrated circuit manufacturing tools capable of operating in parallel on a plurality of semiconductor wafers; (b) a modular optical inspection system; and (c) a handling tool for moving the semiconductor wafers among the plurality of manufacturing tools and the inspection system. The modular optical inspection system may include (i) a plurality of modular inspection subsystems each configured to detect defects on a portion of a semiconductor wafer, and (ii) a mechanism for moving at least one of the semiconductor wafer and the plurality of modular inspection subsystems with respect to one another. Each of the modular inspection subsystems has a field of view spanning a fraction of the width of the semiconductor wafer. Together the subsystems' fields of view cover a substantial portion of the wafer surface.

In operation, the manufacturing system transfers the semiconductor wafer (at some arbitrary point in the fabrication process) from one of the plurality of manufacturing tools to the modular optical inspection system. Then, the inspection subsystem moves at least one of the semiconductor wafer and the plurality of modular inspection subsystems with respect to one another such that each of the modular inspection subsystems inspects, in a single pass across the semiconductor wafer, an associated region of the semiconductor wafer.

The interrelated integrated circuit manufacturing system may be a cluster tool or a phototrack tool for example. In a preferred embodiment, the multi-stage integrated circuit manufacturing system includes a cooling station at which the modular optical inspection system is located. To avoid difficulties associated with introducing the inspection system into a vacuum environment associated with cluster tools and other integrated circuit manufacturing systems, the modular optical inspection system may be located above a window of one of the manufacturing tools (e.g., a cooling stage). Then the system provides the wafer at a location near the window so that the inspection system can take an image.

Another aspect of the invention provides a modular optical inspection subsystem as described above—although not necessarily used with a multi-stage manufacturing system—but including a translatable Fourier filter system. The Fourier filter system may include the following features: (a) a translatable medium having transparent regions and opaque regions in fixed spatial relation to one another and defining multiple Fourier filters; and (b) a translation mechanism arranged to translate the translatable medium such that individual Fourier filters are presented for filtering light. In one embodiment, the translatable medium is a tape that may be wound on rollers (or reels) or a continuous loop.

The translatable medium may assume various configurations. In one case, the spacing between the opaque regions varies substantially continuously over at least a segment of the translatable medium defining at least two Fourier filters. Alternatively, at least a segment of the translatable medium is divided into discrete Fourier filters. The translatable medium may be made from etched metal, metallized transparent plastic, etc. In some embodiments, parallel strips define the opaque regions. This is most appropriate for an etched metal design. In other embodiments—appropriate for the metallized plastic construction—the opaque regions may comprise discrete spots.

The translation mechanism may include any components suitable for translating the medium to present differing Fourier filters to a Fourier image plane in a modular inspection subsystem. For example, the mechanism may include an actuator (preferably only one), a mechanism arranged to engage an actuator, a roller which rotates under torque from the actuator, etc.

In another aspect of the invention, a modular optical inspection system as described above may employ time-delay integration to facilitate rapid imaging. In such systems, at least one of the plurality of modular inspection subsystems includes (a) a two-dimensional sensor configured to receive light from the surface of the semiconductor wafer; and (b) a controller configured to control the relative speeds at which (i) data is read from the sensor and (ii) the modular inspection subsystem and the semiconductor wafer are moved with respect to one another. In operation, the controller causes one row of pixel data to be read from the two-dimensional sensor each time the at least one inspection subsystem moves by one pixel length with respect to the semiconductor wafer. The two-dimensional sensor may be a CCD array, for example.

Yet another aspect of the invention provides a particular data processing system for the modular optical inspection system as described above. In this case, the inspection system may include (a) a master processor configured to process data delivered from at least some of the modular inspection subsystems and (b) a local processor provided with a first one of the plurality of modular inspection subsystems and configured to process data collected by the first modular inspection subsystem. Typically, the master processor is connected to and directly communicates with each of the separate local processors. In a preferred embodiment, the local processor is a digital signal processor. Regardless of the class of processor, the local processors may implement an algorithm that distinguishes valid pattern scattering from defect scattering on the semiconductor wafer.

The features and advantages of this invention may be further appreciated with reference to the following detailed description and associated drawings.

BRIEF DESCRIPTION OF THE DRAWINGS

The accompanying drawings, which are incorporated in and constitute a part of this specification, illustrate several embodiments of the invention and, together with the description, help to explain the principles of the invention.

DETAILED DESCRIPTION OF THE PREFERRED EMBODIMENTS

Presently, preferred wafer-inspection systems, in accordance with the present invention, will be described below making, reference to the accompanying drawings. It should be understood that the invention is not limited to these embodiments which are provided to present certain aspects and examples of the invention. It should be understood that while the methods and apparatus presented herein cover systems for imaging a patterned semiconductor wafer, they could also be employed to image rough films, unpatterned semiconductor wafers, backsides of wafers, photomasks, reticles, flat panel displays such as LCDs, etc.

Figure 1:
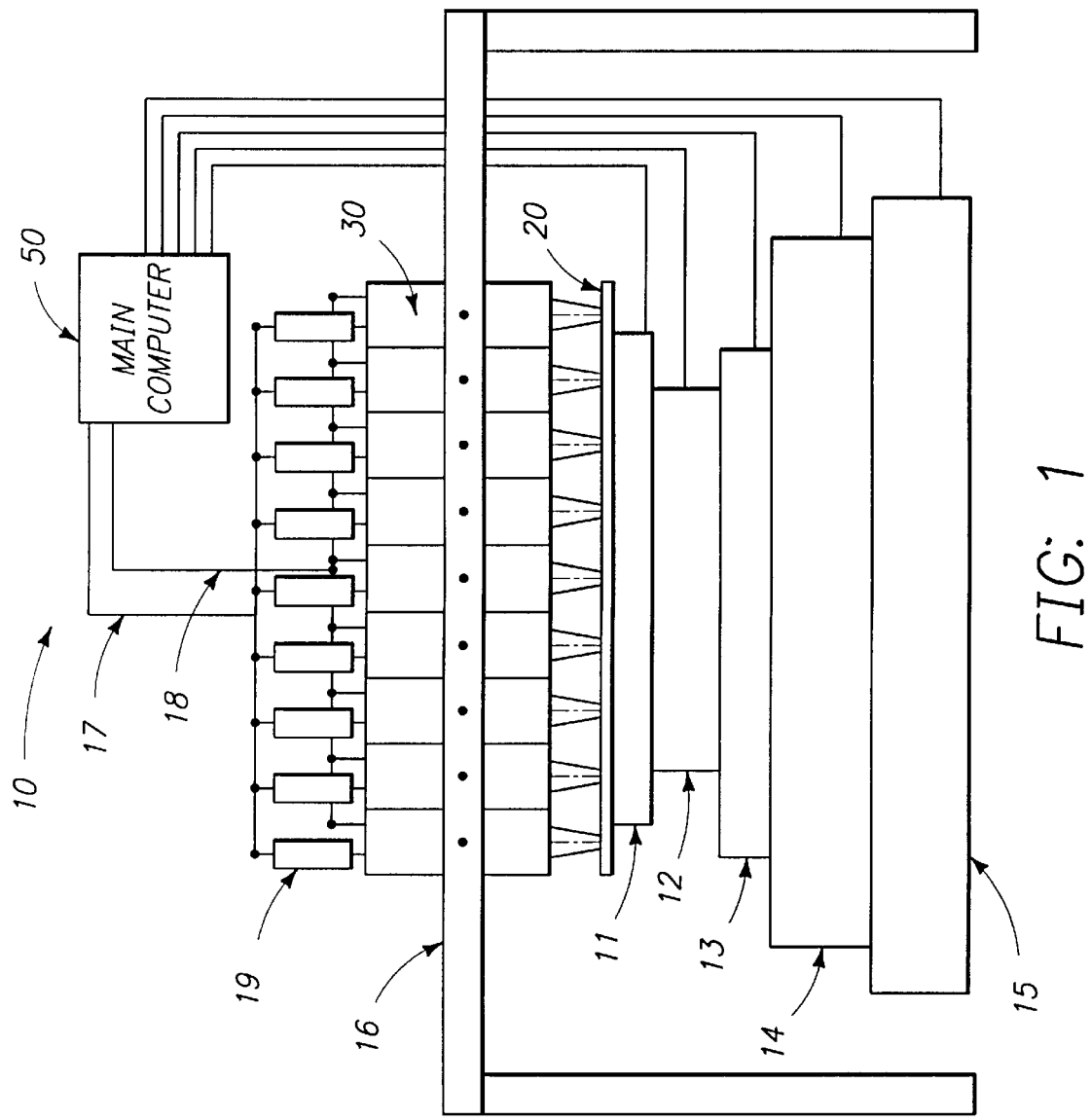
FIG. 1 is a block diagram of a modular inspection system of the present invention.
Figure 2:
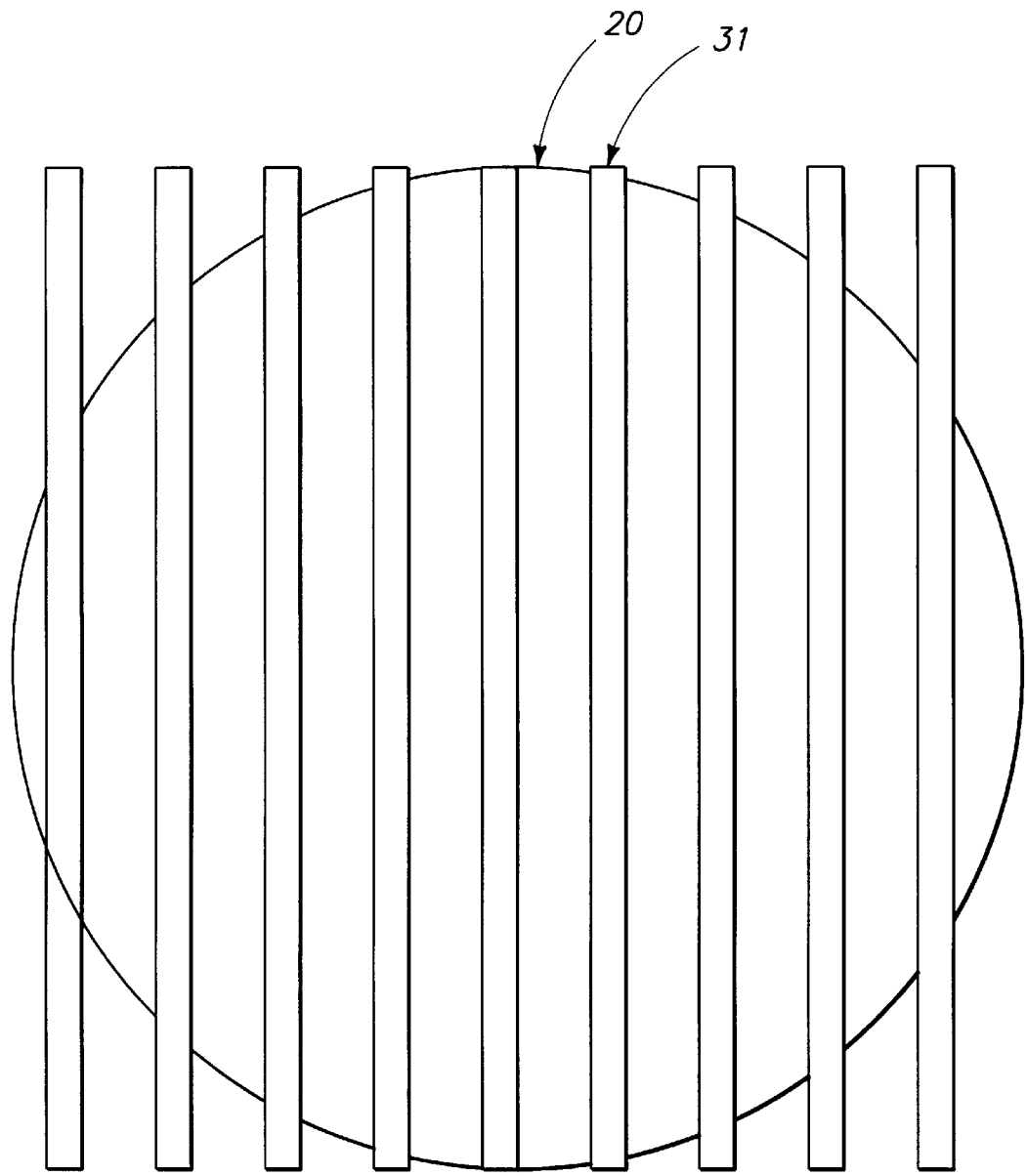
FIG. 2 is a diagram of the measurements swaths for a plurality of optical subsystems analyzing a semiconductor wafer, in accordance with an embodiment of this invention.

FIG. 1 shows a block diagram of a system 10 of a preferred embodiment of the present invention. System 10 includes a plurality of imaging subsystems 30. The imaging subsystems 30 work in parallel, each simultaneously analyzing a portion of a wafer 20. The imaging subsystems 30 are kinematically supported over wafer 20 by a supporting structure 16. As portions the length of the wafer are imaged, the wafer is shifted widthwise under the optical subsystems to image another set of portions, until the entire wafer is imaged. FIG. 2 illustrates the scans 31 of each optical subsystem 30 on a wafer 20 during a single pass. Following a single pass, as illustrated in FIG. 2, the wafer is indexed sideways by one optical subsystem field-of-view and another set of scans 31 is made parallel to the previous set of scans. This process is repeated until the entire wafer has been covered by the scans. It should be understood that if the field of view for each optical subsystem is sufficiently wide, only a single pass is required to image the entire wafer.

In the preferred embodiment, each module is connected to image-processing logic implemented on a local processor or board 19, which is in turn connected to a motherboard or main computer 50. In one embodiment, each board 19 includes a digital signal processor (DSP). Preferably, image-processing logic on board 19 handles at least some of the image-processing computations for the image within the field-of-view for the associated optical subsystem. Of course, other image-processing arrangements are feasible. For example, a single larger image computer may receive and process all the signals coming from the modules 30 rather than having a separate image-processor for each module.

Figure 4:
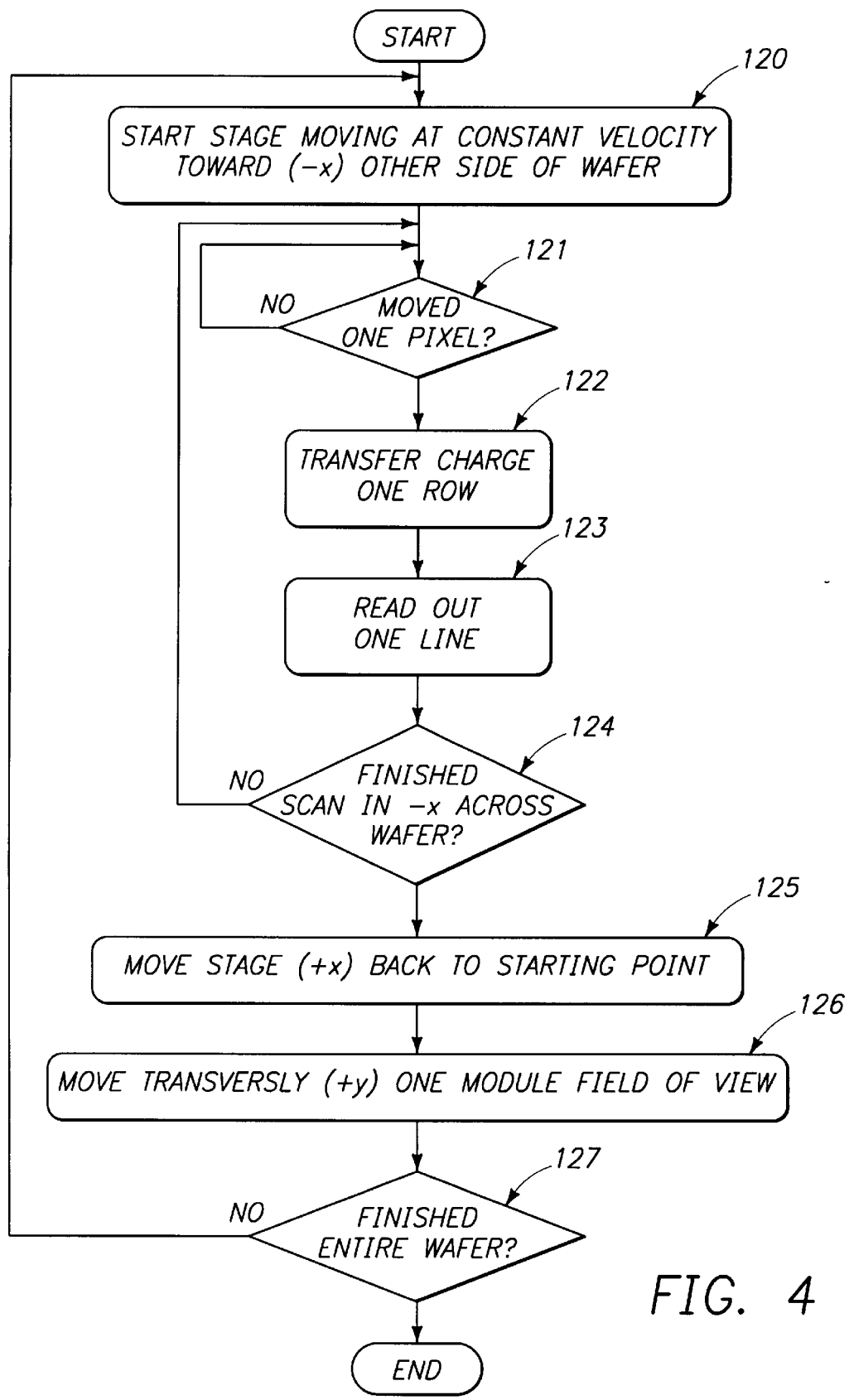
FIG. 4 is a flow chart presenting steps that may be used to scan a wafer in accordance with a time-delay integration procedure of this invention.

Each subsystem 30 and local processor 19 is connected to a master control computer 50 to upload and download pre-processed information. Among other possible functions, the master control may download programs via a wire 17 and upload defect reports via a wire 18, and may maintain aggregate defect databases and implement interfaces for the system operator to command the inspection operation. It may also direct the location of wafer 20 relative to optical subsystems 30 by a stage 15, which is synchronized with the imaging subsystem as shown in FIG. 4.

In FIG. 1, the wafer 20 is held in place with a vacuum or electrostatic chuck 11. Chuck 11, which may be fabricated by lapping a metal surface flat, constrains the wafer, when vacuum is applied, to be flat also. The chuck is supported by a rotation stage 12 which is used to rotate wafer 20 such that the valid wafer structure is orientated parallel to the stage scan direction. Valid wafer structures may occur in large repetitive patterns such as dies, cells, or other surface structures on a wafer surface. Often a wafer surface is characterized by dies separated by narrow blank separations which collectively resemble a city street map when viewed from above, i.e., blocks (dies) bounded by streets (blank areas between dies). This arrangement of orthogonal lines on a wafer is sometimes referred to as a "Manhattan" geometry and is found on many patterns within a die, typically patterns associated with memory elements and logic currents.

Various known algorithms can be used to determine if the wafer die structure is parallel to the scan direction for example, an image of the structure on one side of the wafer can be compared with another image of identical structure taken on the other side of the wafer and by rotating the wafer so that the difference between the patterns can be minimized to align the wafer's structure to the scan direction.

Rotation stage 12 is supported by a leveling mechanism 13. The leveling mechanism is used to alter the plane of the surface of the wafer to be parallel to the plane of the foci of the optical subsystems (modules) 30. This assures that all optical subsystems are in focus while the wafer is scanned by them. Focus or proximity sensors can be applied to determine when the wafer surface is parallel to the modules' foci. Alternatively, optical autofocus mechanisms can also be used. And, for some low resolution applications, depth of focus can be arranged to be large enough that leveling is not required.

The leveling mechanism 13 is supported on a pair of motion stages (14 & 15) for x and y movements of the wafer under the modules. The stage for x-motion 15 is used to pass the wafer under the modules to create the examined scans 31 seen in FIG. 2. The stage for y-motion 14 is used to move the wafer sideways a distance equal to the modules' fields of view so that another x-pass can take place parallel to the previous set of scans. Depending upon the modules' fields of view, one or more x-passes may be needed to cover the wafer. In the preferred embodiment, the modules' fields of view are 4.4 mm, thus 5 swaths are required to examine the entire 200 mm wafer's surface (5×4.4=22 mm across covered by each module; nine modules×22 mm=198 mm (outer mm radius of wafer is not tested)). Thus, the x-stage will move 200 mm (the length of a pass) five times and the y-stage will move 4.4 mm five times (total motion in y is 22 mm).

In previous systems employing a single optical system, the system must index across the whole wafer, taking a single image swath at each pass. In contrast, in the system of the present invention, multiple subsystems simultaneously image multiple swaths during each pass across the wafer. The wafer is then shifted so that new swaths may be imaged. Thus the entire wafer may be imaged in a small percentage of the time required by a single optical system.

Figure 3:
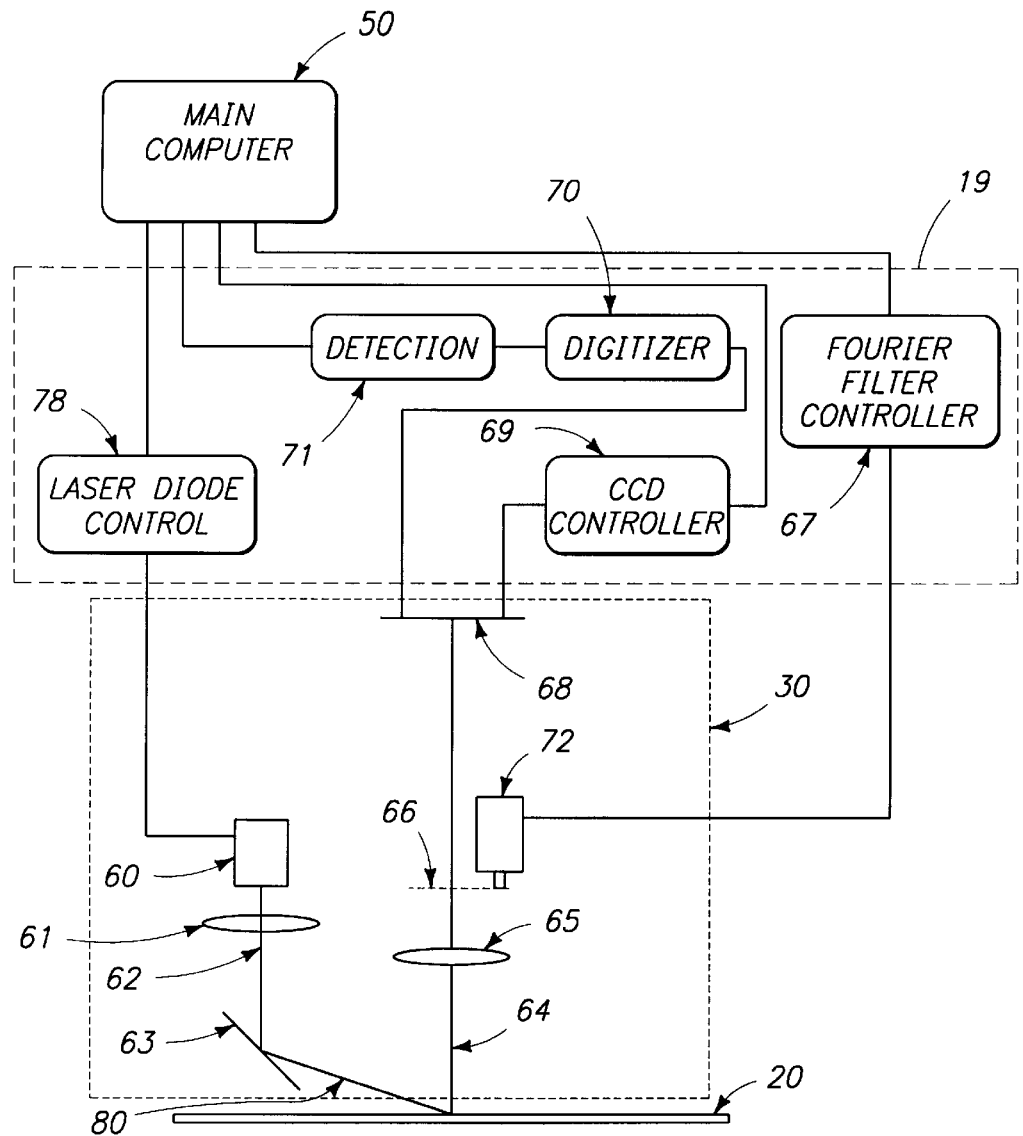
FIG. 3 is a diagram of an optical-inspection subsystem suitable for use with the modular inspection systems of this invention.

FIG. 3 shows a block diagram of an imaging subsystem 30 of the present invention and an associated board 19. An illuminator 60 (preferably a monochromatic coherent-light source) provides light to location control 61 for illumination of an area of the wafer via path 62. Computer 50 controls the illumination level via a controller 78. In one example, illuminator 60 may be a high-intensity laser diode, such as those used in common laser-pointing devices or compact-disk applications. While currently available diode lasers typically operate in the red and infra-red regions of the electromagnetic spectrum, it will, in some embodiments, be desirable to employ light sources having shorter wavelengths for applications relying on scattered light. This is because scattering efficiency is proportional to the inverse of wavelength to the fourth power. Thus, it will generally be desirable to employ illuminators producing radiation of wavelengths not greater than about 500 nanometers. Examples of other suitable illuminators include helium neon lasers, argon lasers, frequency doubled YAG lasers, frequency tripled YAG lasers, excimer lasers, etc.

The light from illuminator 60 is shaped (e.g., collimated) and directed by a location control 61, which may include lenses, diffractive-optical components, filters, and/or mirrors. In a preferred embodiment, location control 61 is a collimating lens which fully collimates the light from a laser diode 60 along a path 62 which reflects off a folding mirror 63 to a portion of the wafer's 20 surface along a path 80. Preferably, the light is directed at a low elevation, or illumination, angle towards the wafer. The illuminated region is chosen to correspond to the location and size of the field of view of a collecting lens 65 and the area of a detector 68.

Preferably, the system is operated in a manner allowing detection of light scattered from defects and features on the wafer surface and blocking light reflected from plane surfaces on the wafer. As mentioned, this is a darkfield illumination. The illumination angle, polarization, and azimuth of the illumination beam incident on the wafer in such directed-darkfield illumination determines the sensitivity of the system to various types of defects which may be present on the wafer. For example, low angle illumination is preferred when looking for particles on the wafer's surface, while higher angles of incident illumination are preferred for particles located in structures below the wafer's surface. In one embodiment, the illumination angle may be varied by changing the angle of mirror 63 relative to the laser light path 62 and/or the plane of wafer 20. Alternatively, additional optical components, such as mirrors and lenses, may be used to facilitate these angle of illumination changes.

As described in U.S. patent application Ser. No. 08/904,892 filed Aug. 1, 1997, naming G. Zhao, S. Stokowski, and M. Vaez-Iravani as inventors, and entitled "SYSTEM FOR DETECTING ANOMALIES AND/OR FEATURES OF A SURFACE," light from the illuminator may be directed onto the wafer surface at an oblique angle in order to illuminate a linear region of the surface. The Ser. No. 08/904,892 patent application is incorporated herein by reference in its entirety and for all purposes. In a specific example, the linear illuminated region has a length of about 5 mm and a width of about 10 μm. The light scattered from the wafer's surface is collected by a lens system viewing the wafer at an elevation angle that is not near the surface normal and an azimuth of about 90 degrees to the incoming illumination. The illuminated linear region on the surface is imaged onto a linear detector array. In this manner, sensitivity to certain defect types is improved and sensitivity to very small particles (<0.2 μm) is increased significantly over viewing the surface in a near-normal manner. Further, more than one detector may view the illuminated linear region on the surface. For example, two or more detectors can view the illuminated region having symmetrical elevation angles on opposite sides of the illuminated region. Using more than one detector increases the defect capture rate and can be used to discriminate defect types based upon the ratios of the detected signals. In the same manner, more than one illumination source at a different illumination angle can be used for increased capture rate and discrimination benefits. In one embodiment, the detectors are located at angles corresponding to high scattering efficiency for surface particles.

Components, such as one or more waveplates, may be provided in the optical path to control the polarization of the light as necessary for a particular application. The signal-to-noise ratio can be dramatically improved by altering the incident light's polarization for particles located on different types of wafer surfaces.

To attenuate unwanted reflections caused by pattern edges of valid structures, the illumination's azimuth angle may be chosen so that the edges are orthogonal to the illumination angle. Thus, the illumination angle should be chosen so that it is not perpendicular to any edge on any valid surface structure on the wafer. In the case of a wafer having only Manhattan type streets, any one of four illumination angles optimally attenuate background reflection. These angles are 45°, 135°, 225°, and 315° with respect to one of the street directions. Such azimuthal angles may be obtained through aiming of the light path 62 such that the light is incident on the wafer 20 surface at the desired angle. In some modern wafer designs, routing lines or other structures are present at 45° with respect to other valid features. In such cases, the azimuth angle should not be orthogonal to these 45° features. Thus, the azimuthal angle should be in a range located midway between the Manhattan streets and the 45° routing lines (or other features). Such angles may be, for example, 22.5°, 67.5°, etc. with respect to the Manhattan streets.

As mentioned, the imaging subsystems of the present invention can operate using directed darkfield-illumination techniques. Darkfield techniques can easily provide a pixel-to-defect detection ratio of 10:1 for non-planar defects, translating into a 100:1 reduction in image-processing requirements for a given inspection time per wafer. The described system could also operate in brightfield mode, although pixel-to-defect ratios would be approximately 1:1 or 2:1, limiting the sensitivity of the system to larger defects such as particulates, but allowing the detection of broad classes of planar defects not seen with darkfield systems such as tungsten puddles, water marks, etc. Illumination can be coherent or incoherent, but coherent monochromatic illumination is preferred due to the possibility of filtering out periodic structures using Fourier techniques as described below. Examples of incoherent light sources include arc lamps, gas discharging lamps, incandescent lamps, and the like. Examples of coherent light sources include diode lasers, Helium Neon lasers, Argon lasers, frequency doubled YAG lasers, and the like.

In FIG. 3, collecting lens 65 may be an imaging lens that collects light scattered by structures and defects on the surface of wafer 20 and images them onto the detector 68 via light path 64. Lens 65 produces a Fourier image plane, where the Fourier transform of the object's diffracted light is visible. The Fourier image plane is located at the rear focal plane of the collecting lens 65 which focuses light which appears to come from infinitely far away. A filter 66 is inserted at this plane to block a particular spatial periodicity corresponding to the periodicity of structures on the illuminated selected area of wafer 20. As shown, the filtered light continues to sensor 68 from the Fourier filter along path 64.

The Fourier filter should be located at or near the Fourier image plane within a depth of focus of the lens system at that point. However, if the light incident on the wafer is not collimated, then the Fourier transform of that light is similarly defocused and is imaged at a plane not technically the Fourier plane, although the filtering function can occur equally well at that location. The defocus of the image will follow the standard leans maker formula:

$1/f = 1/\text{object distance} + 1/\text{image distance}$; $f$=focal length of the lens system where the object distance represents the location where the non-collimated light comes to a focus, whether real or virtual.

When coherent light is incident on a periodic structure like an array on a wafer, the light is diffracted from the structure and, because of interference in the light leaving the structure, produces a diffracted pattern resembling a series of focused points or lines in the Fourier image plane. The focused points sometimes line up on vertical or horizontal bands, which bands are separated from one another by distances dictated by the spacing(s) of the repeating features on the semiconductor wafer surface. More specifically, the spacing of the focused points is a function of the wavelength of incident light, the spacing of the wafer's array structure, and the focal length of the collecting lens such that:

Fourier filter spacing=Focal length*wavelength/Wafer cell size (1)

The Fourier filter contains opaque regions arranged in a pattern corresponding to the pattern of concentrated light scattered from the repeating features on the surface (and governed by equation 1). When aligned properly in the Fourier image plane, the Fourier filter blocks light from repeating valid features of the semiconductor surface, thereby increasing the signal-to-noise ratio for defect detection. Light from non-periodic surface features is typically uniformly distributed over the Fourier plane, so its signal is only slightly reduced due to the blockage from the filter patterns, but the background is substantially reduced.

Figure 5:
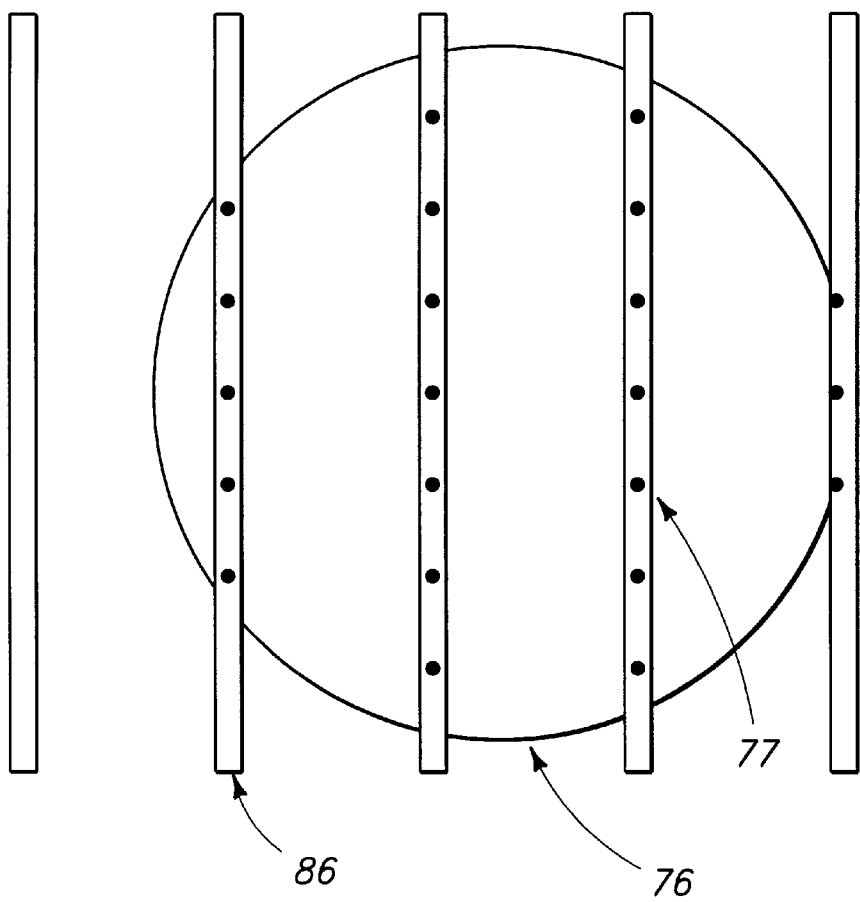
FIG. 5 is a diagram of a Fourier filter positioned in a Fourier image plane to block light scattered from valid repeating surface structures in accordance with some embodiments of this invention.

FIG. 5 illustrates a Fourier image plane 76 and the appearance of diffraction spots 77 of the Fourier pattern produced by an array structure from a wafer. Opaque bands 86 at the Fourier image plane are used to block the light in the spots 77 of the Fourier pattern from proceeding to the detector. Blocking this light eliminates the light diffracted from the valid wafer array structures, but passes light scattered from defects which are not periodic. Thus the signal-to-noise ratio is increased, facilitating the detection of defects.

Figure 6:
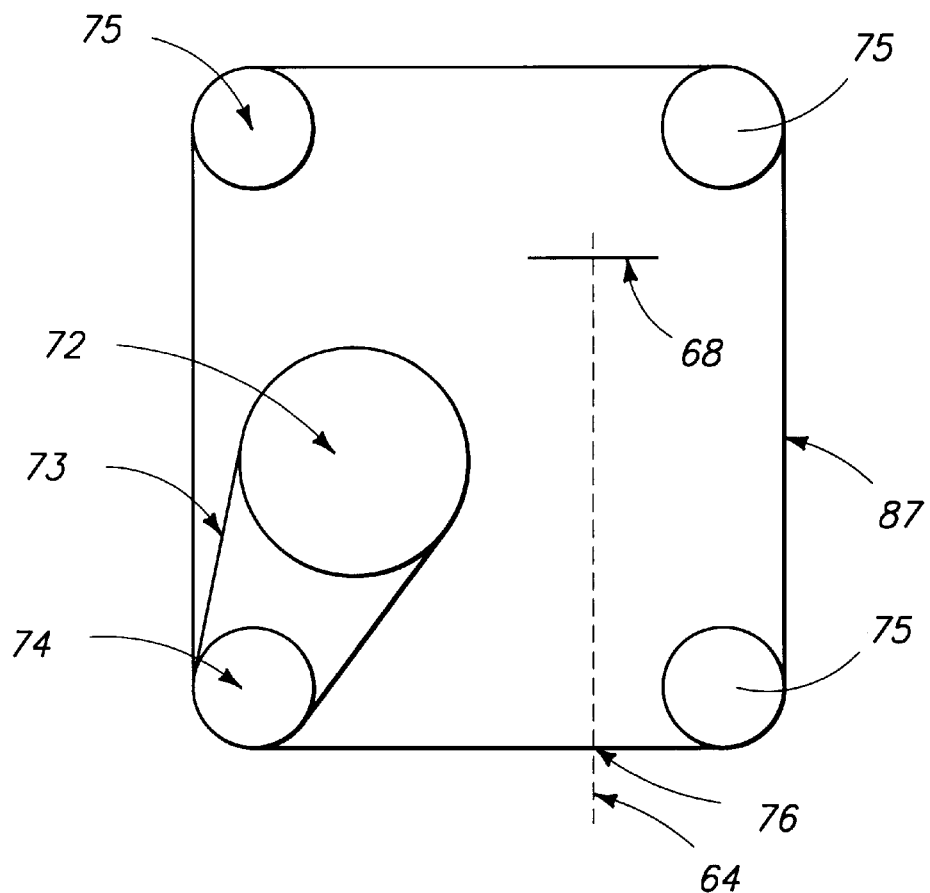
FIG. 6 is a diagram of a Fourier filter transport mechanism in accordance with an embodiment of this invention.

The wafer's cell size is variable depending upon the type of die structures provided on the wafer and the manufacturer's specifications. Thus, the pitch or period of the spacing of the diffracted spots at the Fourier plane assumes different values for different wafer array structures. As a consequence, the filter spacing must be adjusted from wafer type to wafer type. In the present invention this can be accomplished with a mechanism as illustrated in FIG. 6. There, a plurality of filters 66 are provided on a tape 87. Each filter on tape 87 contains blocking structures of a pitch appropriate for a particular valid die pattern. The filters are transported to the Fourier image plane 76 so that the correct pitch is present to correspond with the currently inspected wafer's cell size.

Actuator 72 (also shown in FIG. 3) with belt drive 73 on drive pulley 74 moves the continuous tape containing the various pitch patterns. Rollers 75 constrain the motion of the tape within the module. Computer 50 controls actuator 72 by a controller 67 to select and transport the portion of the Fourier filter tape having the proper pitch and to properly place it at the Fourier plane. Since the location of the pattern within the Fourier plane can vary, this placement includes properly aligning the tape with the Fourier pattern of the currently inspected wafer location. Thus, both selection of the proper pitch as well as proper alignment are performed using a single actuator. In a preferred embodiment that single actuator is a stepper motor.

Figure 7A:
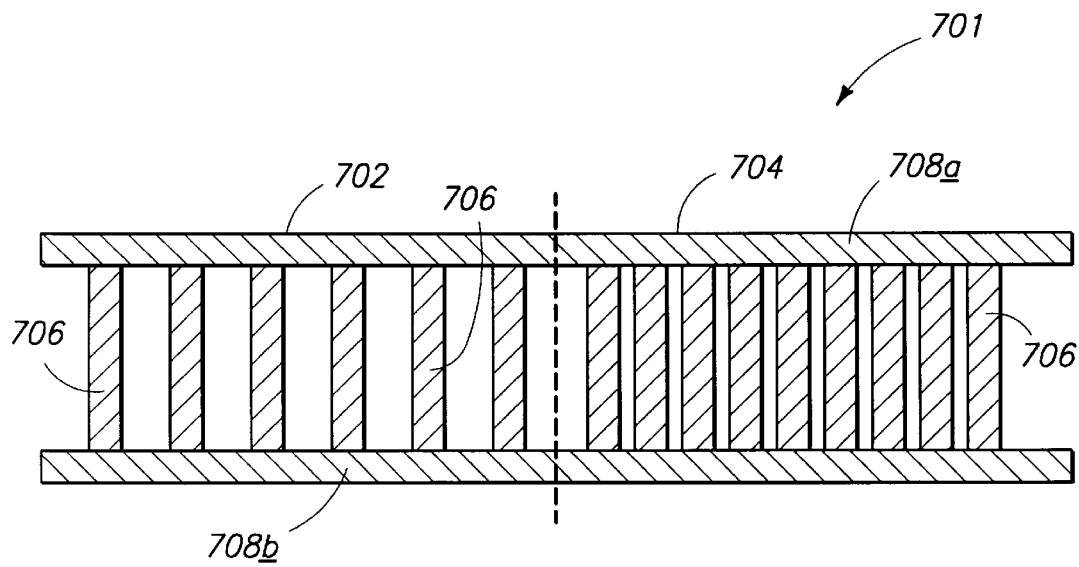
FIGS. 7A–7E are diagrams of various tapes defining multiple Fourier filters for use with this invention.
Figure 7B:
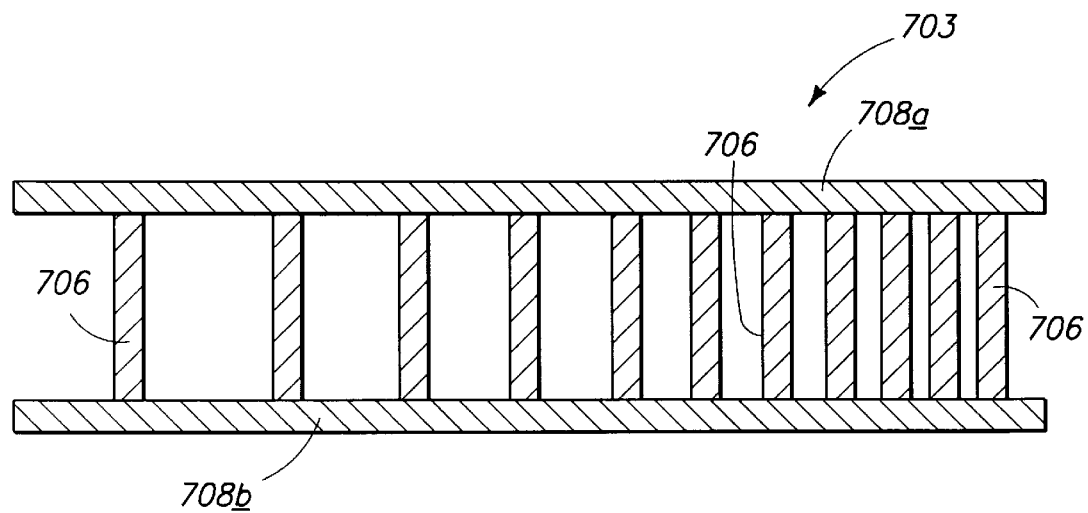
Figure 7C:
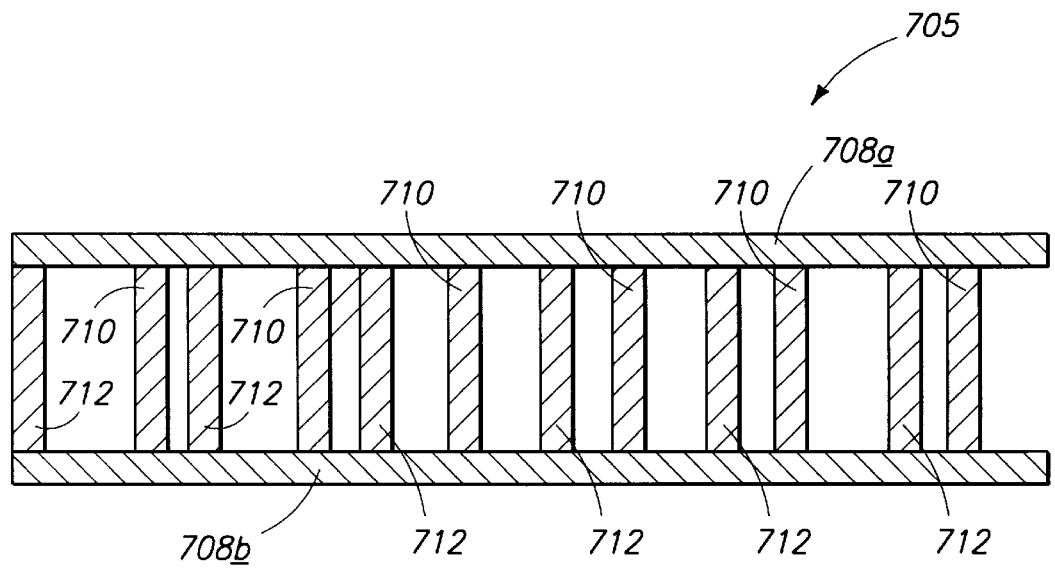

The Fourier filter may be constructed in various manners. In one preferred embodiment, the filter is constructed from a strip of thin metal (e.g., Copper-Beryllium) having an etched pattern of holes or apertures of various periodicities, as shown in FIGS. 7A–7C. The relative locations where the metal remains after etching are chosen match the relative locations of light in Fourier image plane that has been scattered from valid repeating structures on the wafer surface. Often, the metal in the etched filter will be shaped as bands or L-shaped regions.

In an alternative embodiment, the Fourier filter takes the form of a transparent material section having opaque regions formed thereon. As in the case of the etched metal, the opaque regions correspond to the locations of the concentrated light in the Fourier image plane that has been scattered from the regular features. The transparent material may be thin, optical-quality Mylar for example. Because the transparent material supports the opaque regions, the opaque regions need not be bands or L-shaped regions connected to continuous metal regions. Rather, they may be dots or other shapes matching the concentrated light reflected or scattered from regular features.

In one embodiment, the filter tape design is fabricated to include discrete filters or filter regions, each specifically patterned to match one or more particular wafer periodic structures. In this case, each discrete filter on the tape includes a particular filter spacing to be used for each specific wafer or intra-wafer structure. And, the spacing of the wires in each discrete filter is a constant predicted by equation 1. In this embodiment, the only adjustment for each wafer (or wafer region) would be the position of the tape so it blocks the Fourier pattern.

FIG. 7A illustrates one embodiment of a Fourier filter tape in accordance with this embodiment. As shown, a Fourier filter tape 701 includes a first region 702 and a second region 704. Both of these regions include opaque vertical metal strips 706 forming a ladder arrangement with continuous horizontal support strips 708a and 708b. Filter tape 701 is preferably formed of thin etched metal.

Note that in filter tape 701, the strips 706 within region 704 are spaced relatively close together in comparison to the corresponding strips 706 of second region 702. Thus, first region 702 might be used as a discrete filter for one type of valid regular feature on a semiconductor substrate, while second region 704 could be used as a second discrete for valid regular features having a different periodicity.

During inspection, Fourier filter tape 701 would be translated so that either first region 702 or second region 704 are used as a filter depending upon the type of integrated circuit or portion of an integrated circuit being imaged. Note that different filters may be appropriate for different regions within a particular die. For example, a memory section of an integrated circuit may require one filter spacing, while a cache memory section of the same integrated circuit may require a different filter spacing.

The opaque regions employed in filters of this invention (e.g., filter tape 701) should be sufficiently wide to block most of the light in the Fourier image plane that has been scattered from the repeating valid wafer structures. In a preferred embodiment, the width of the vertical strips or width the opaque spots (see filter tape 707 in FIG. 7E) is between about 0.1 and 0.5 mm. More preferably, the width of the vertical strips is between about 0.3 and 0.4 mm.

FIG. 7B shows a second preferred embodiment in which a Fourier filter tape 703 includes vertical strips 706 spaced in a continuously variable fashion. Filter tape 703 may be used in a manner similar to filter tape 701, but without having discrete filter regions. Rather, a filter having the appropriate spacing of vertical strips 706 for a given application is provided by translating filter tape 703 to a position where the spacing of vertical strips 706 corresponds to the spacing of the concentrated light in the Fourier image plane. As with Fourier filter tape 701, Fourier filter tape 703 is preferably made of etched thin metal strips or alternatively from a metallized transparent substrate such as Mylar.

The spacing between individual vertical strips 706 may follow various mathematical progressions. For example, the spacing may vary logarithmically. In one specific embodiment, the spacing of the wires 706 in continuously variable filter tape 703 starts with a spacing of about 1 mm distance between the first wire (n=1) and the second (n=2). The space to the next wire (n+1) may be determined by the following equation:

$$\text{Distance}_{n=1} = \text{Distance}_n * (1+Q) \tag{2}$$

where Q is about 0.015 in a preferred embodiment. The maximum spacing of the pattern is determined by the aperture size of the Fourier plane such that a single wire could block a Fourier pattern containing a single spot. The total length of the tape is reasonable with about 15 inches being used for the preferred embodiment.

Generally, the spacing of Fourier transform spots in the Fourier plane is essentially equal across the plane. As indicated by equation 2, the wires in the filter increase slightly in spacing across the Fourier plane. Thus, the widths of the wires must be somewhat greater than the spot size at the image plane to account for both the accuracy to which the pattern can be positioned and the spacing difference between the wires across the Fourier plane. In practice, the Fourier image spots are often less than about 0.1 mm in diameter. Further, the positioning accuracy of a Fourier filter can be expected be less than about 0.05 mm. With these criteria in mind, the wire widths in filter tape 703 are preferably between about 0.2 and 0.6 mm. For example, a 0.35 mm wire width leaves about 0.2 mm available for the spacing difference across the aperture. Of course, other configurations having different width wires, spacings or separations, starting spacings, and change in spacings along the tape will have an equivalent effect.

Beyond the filter tape spacings indicated in FIGS. 7A and 7B, more complex patterns are possible (i.e. double periodicity, matched filtering, etc.). For example, FIG. 7C presents double frequency Fourier filter tape 705 for use with this invention. In this case, two groups of vertical opaque strips are provided, each having a distinct spacing frequency. The first frequency is defined by regular spacing between vertical strips 710 and the second frequency is defined by vertical strips 712. Note that the spacing between vertical strips 712 is greater than the spacing between vertical strips 710.

A multiple frequency Fourier filter such as Fourier filter tape 705 is appropriate in the case where the region of the semiconductor wafer being imaged contains two or more overlaid repeating structures. This may be the case when, for example, the source and drain regions of a memory element are separated by a first frequency and the substrate taps in the same memory element are separated by a second frequency. The scattered light from the substrate taps might be blocked by the vertical strips 710, while the scattered light from the source drain regions might be blocked by the vertical strips 712. In another example, a DRAM typically includes multiple lines all of one micrometer thickness. This constant line thickness introduces a fixed frequency component of the Fourier image. The repeating cells within the DRAM introduce a second component of the Fourier image. The components in the Fourier image plane corresponding to these two DRAM features can be filtered by two sets of filter wires, each of different spacing as in Fourier filter tape 705.

It should be understood that while Fourier filter tape 705 is shown as having only two spacings (the spacings between vertical strips 710 and the spacings between vertical strips 712), it may be appropriate to include three or more spacings in the filter.

Figure 7E:
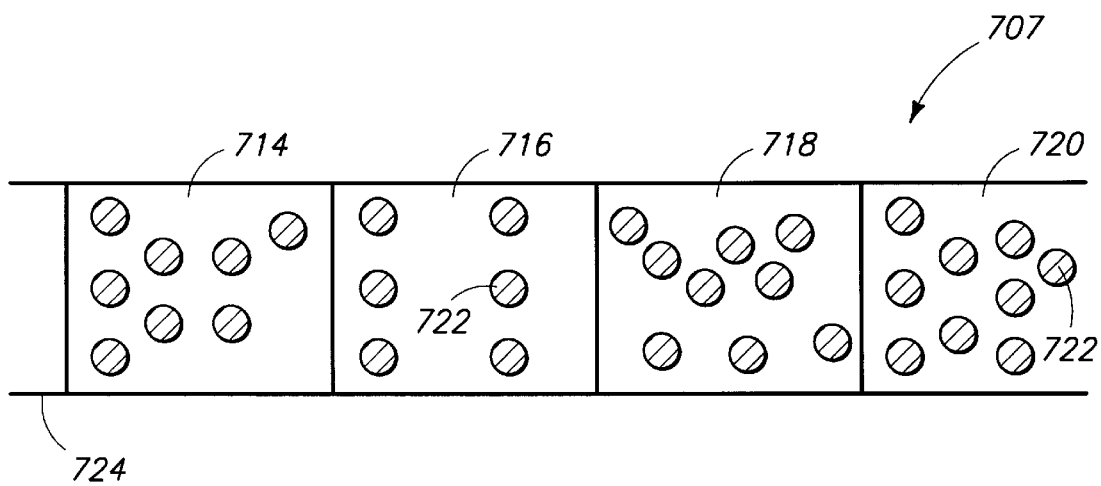
Figure 7D:
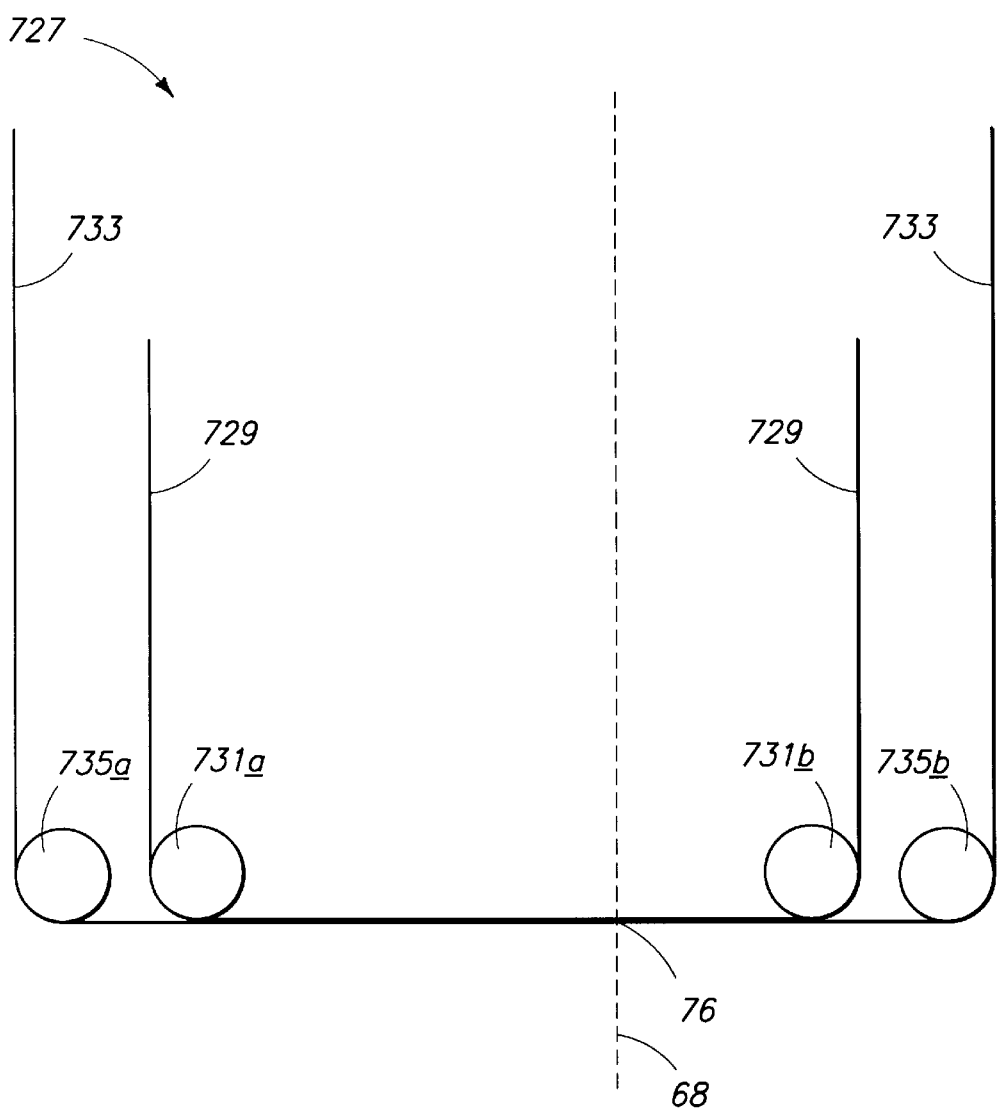

Multiple frequency filters may be implemented with two or more filter tapes as illustrated in FIG. 7D. There a two tape filter mechanism 727 provides overlapping filter tapes at the Fourier image plane 76. A composite filter is provided by overlaying a first tape 729 having a first pattern of opaque regions and a second tape 733 having a second pattern of opaque regions. The desired filter region of first tape 729 is positioned in Fourier image plane 76 by rolling over dedicated rollers 731a and 731b. And a desired filter region of second tape 733 is positioned via dedicated rollers 735a and 735b. In a preferred embodiment, the various rollers are positioned such that first filter tape 729 and second filter tape 733 are separated by no more than about 0.1 to 0.5 mm at Fourier image plane 76 or within the depth of focus at the Fourier plane. To independently control positioning of the first and second filter tapes, it may be desirable to employ a separate actuator for each tape.

FIG. 7E shows yet another Fourier filter tape format. There a filter tape 707 includes discrete filter regions 714, 716, 718 and 720 formed on a transparent medium 724. Each of these regions includes discrete rounded opaque regions 722. It should be understood that in some cases the opaque regions may assume elliptical, rectangular, or other shapes as appropriate to adequately block regular patterns of the Fourier image. The use of isolated opaque regions 722 in tape 707 has the advantage of blocking very little or no scattered light that may contain information about defects.

Another advantage of the structure employed in filter tape 707 is that it allows a two-dimensional filter. In FIG. 5, spots 77 are aligned along lines of constant spacing. This is a one-dimensional pattern in the Fourier image plane. Some more complicated (less regular) valid wafer patterns, generate two-dimensional patterns of scattered light in the Fourier image plane. In such cases, the Fourier image plane components to be subtracted out do not all fall in a regular vertical bands as shown in FIG. 5. In such cases, there may be other Fourier spots to be subtracted that reside between such regular strips. While such two-dimensional components can be removed in an etched metal filter employing H-shaped or L-shaped structures, it will often be more convenient to simply put metalized dots at the appropriate locations in two-dimensions on a transparent medium as shown in regions 714, 718, and 720 of filter tape 707.

One potential problem with filters is diffraction of light passing by "hard edges" which create image plane artifacts like image blurring in a particular direction. Hard edges are generally sharp boundaries between opaque and transparent regions. Various techniques (e.g., apodization) may be employed with this invention to reduce the detrimental effects of hard edges. Specifically, steps may be taken to soften edges between opaque and transparent regions. One way this is accomplished is by gradually reducing the thickness of an opaque spot provided on a transparent medium. Many deposition techniques naturally accomplish this. With respect to etched metal, it is not so easy to gradually decrease the metal thickness near the edge. However, an etched metal edge can be made "softer" by making the edges serrated.

Figure 8:
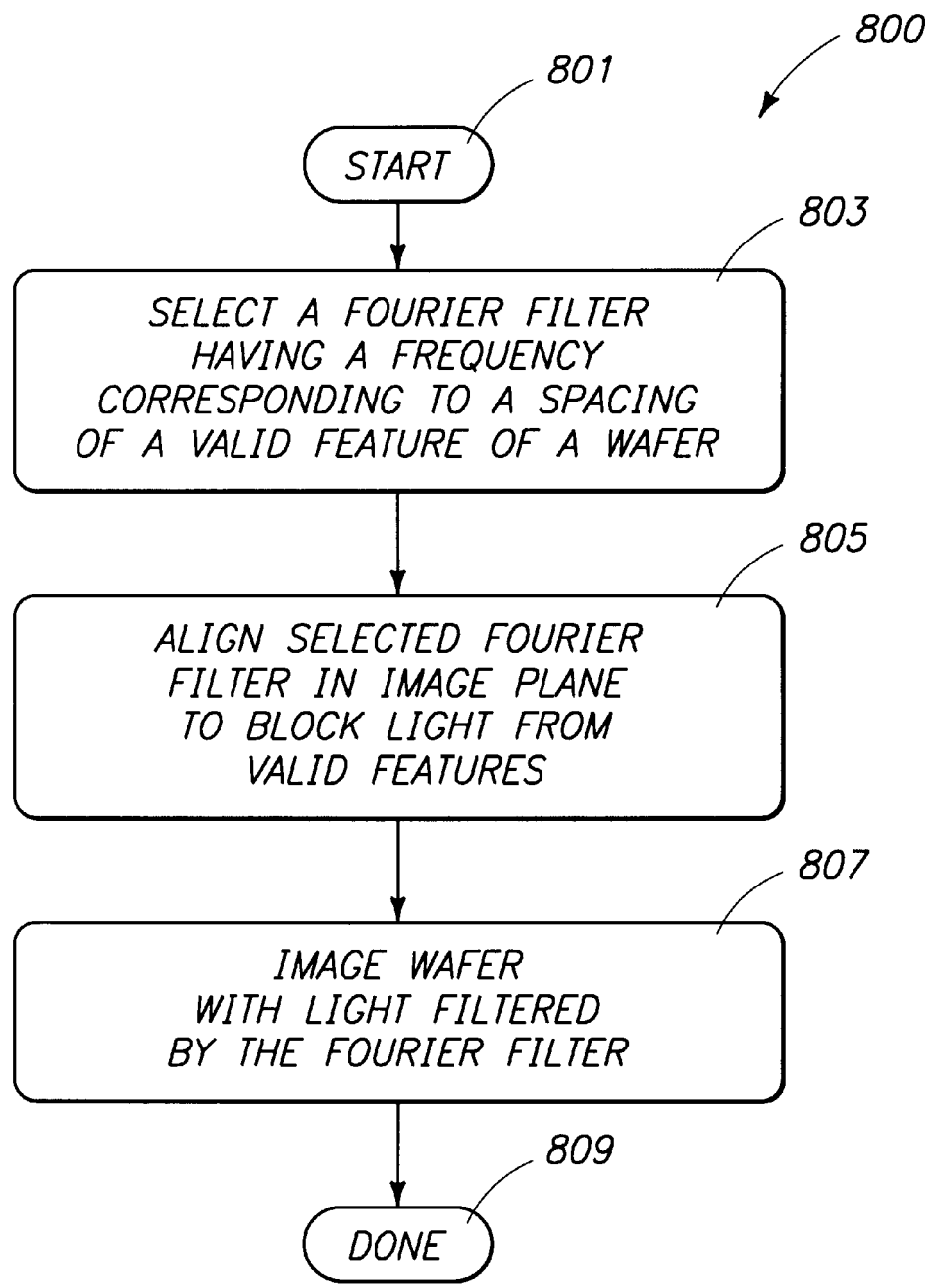
FIG. 8 is a process flow chart depicting some steps in Fourier filtering an image.

FIG. 8 is a process flow chart presenting three important steps in a filtering technique 800 in accordance with this invention. Process 800 begins at 801 and in a step 803 the inspection system selects a Fourier filter having a frequency corresponding to a spacing in the Fourier image plane of light scattered from valid features of the wafer being inspected. As explained above, valid features have many possible different patterns on semiconductor wafers. Therefore, it is necessary to select a Fourier filter which blocks only light corresponding to the Fourier transform of the valid features in the region of the wafer under consideration.

After the appropriate filter has been selected at step 803, the inspection system next aligns that selected Fourier filter in the image plane at a step 805. The system aligns the filter so that it blocks only light from valid wafer features. An important component of alignment step 805 is arranging opaque features of the selected Fourier filter to be in phase with light from the wafer surface.

After the inspection system properly aligns the Fourier filter, it images the wafer at a step 807 with light from the wafer that has been filtered by the selected Fourier filter. Thereafter, the process is completed at 809.

Figure 9A:
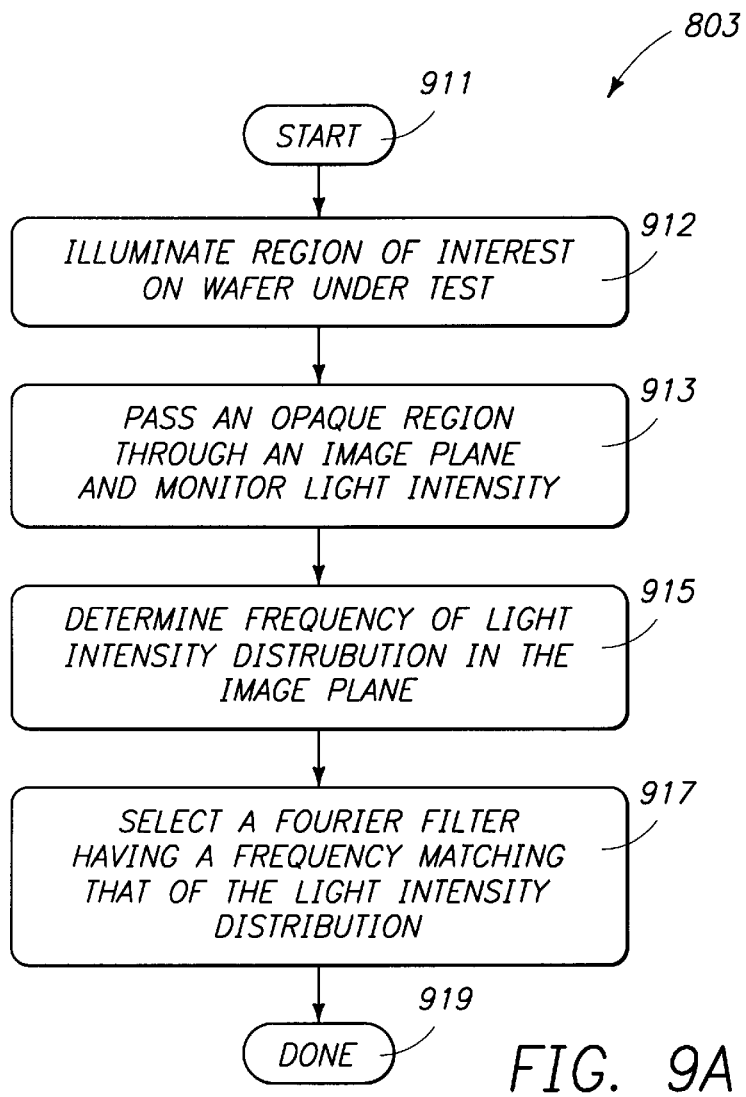
FIG. 9A is a process flow chart illustrating some steps that may be employed to select a suitable Fourier filter in accordance with one embodiment of this invention.

A preferred process of selecting a Fourier filter having the appropriate frequency (step 803 of process 800) is depicted in FIG. 9A. As shown there, process 803 begins at 911 and then, at a step 912, a region of interest in the wafer under test is illuminated with light from source 60. This light scatters of the wafer surface and is directed to sensor 68. At a step 913, the inspection system passes an opaque region (or a slit) through the Fourier image plane (of the light scattered off the wafer surface) and monitors the light intensity as a function of the position of the opaque region (or slit). Then, at a step 915, the inspection system determines the frequency of the light intensity distribution in the image plane as monitored in step 913. Finally, the inspection system selects a Fourier filter having a frequency matching that of the light intensity distribution determined at step 915. The process is then concluded at 919.

Figure 9B:
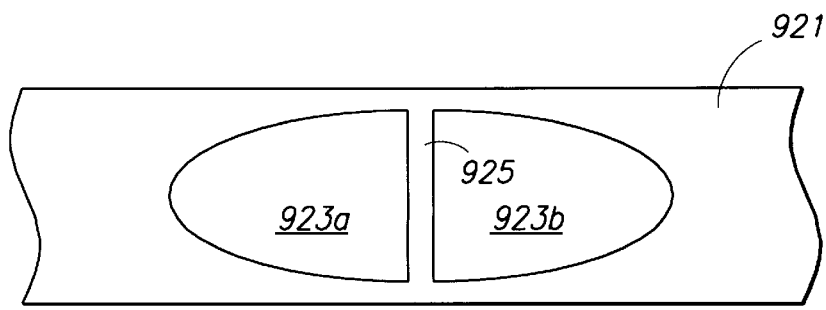
FIG. 9B is an illustration of a tape section including an opaque strip employed to identify proper spacing of a Fourier filter to be used during inspection of a wafer or wafer subsection.

FIG. 9B shows an appropriate section of a tape 921 which may be translated in order to perform step 913. Specifically, tape 921 includes two transparent regions 923A and 923B straddling an opaque region 925. During process step 913, tape 921 is translated so that opaque region 925 moves across the image plane. All the while, light passing through transparent regions 923A and 923B is monitored at a sensor disposed downstream from tape 921. In a preferred embodiment, tape 921 also contains the various Fourier filters which are ultimately used to image a wafer.

Figure 9C:
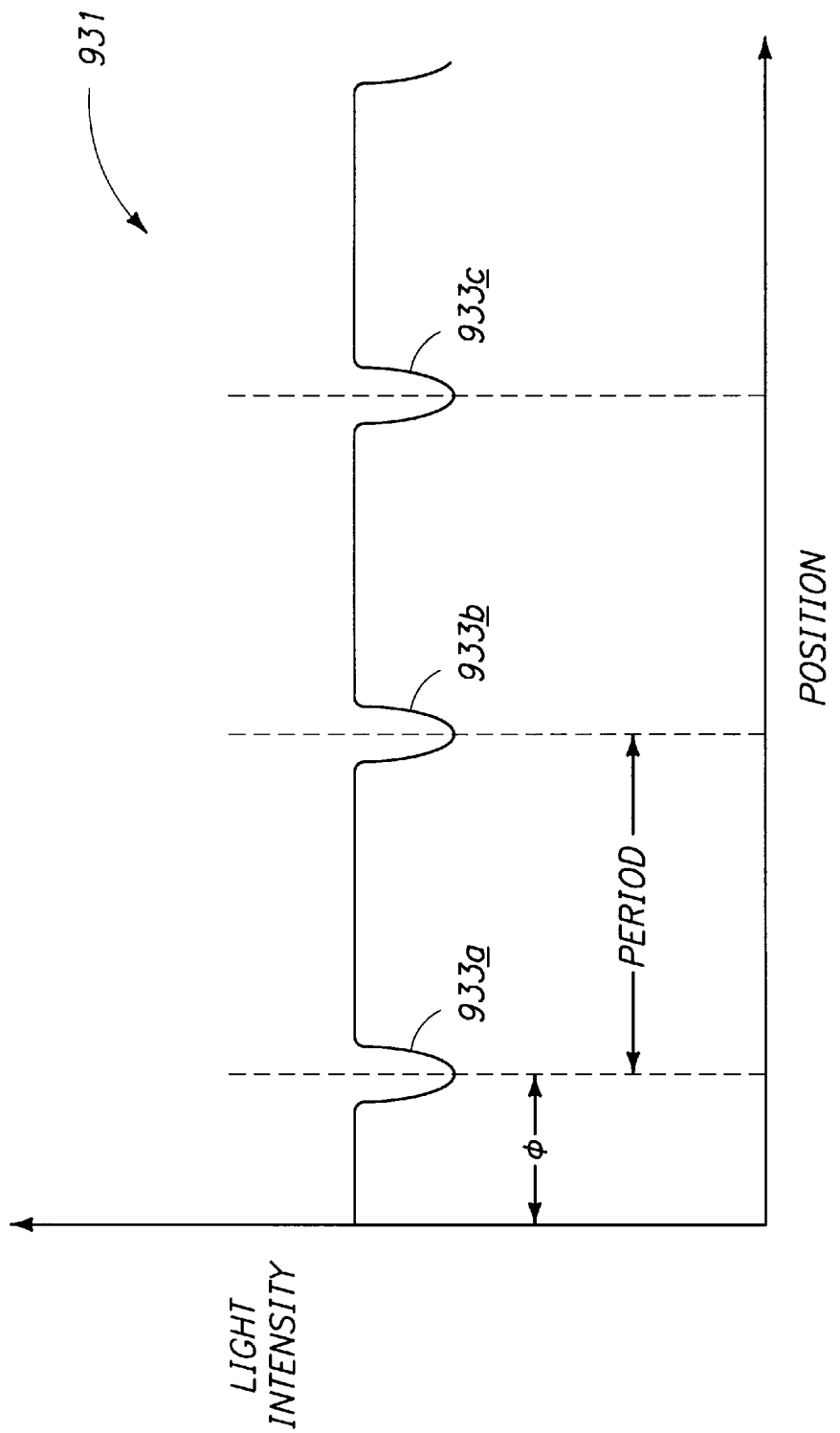
FIG. 9C is a hypothetical plot of light intensity versus position in a Fourier image plane, which plot may be employed to select a Fourier filter of appropriate spacing.

FIG. 9C presents a hypothetical light intensity distribution 931 which plots light intensity as a function of the position of opaque region 925. As shown, distribution 931 includes troughs 933A, 933B, and 933C of approximately equal separation distance. This separation distance corresponds to the period of light in the Fourier image plane which has been scattered from a valid repeating wafer structure. This period specifies the frequency of the Fourier filter ultimately selected to be used during imaging of the wafer. The first intensity trough 933A is located at a distance from the origin specifying the phase φ of the light intensity distribution. This phase is used to align the Fourier filter at the proper location within the image plane. If the period and phase information are provided by passing a slit (rather than an opaque strip) through the Fourier image plane, the light intensity distribution will appear as a series of peaks (not troughs).

In one embodiment of the present invention sensor 68 is a frame transfer CCD working in a time-delay integration (TDI) mode. High-performance, low-cost two-dimensional CCD arrays are available that permit TDI operation with low-noise operation and excellent quantum efficiency in the red region of the spectrum where many laser diodes produce their light. For example, such operations are described in U.S. Pat. No. 4,877,326 issued to Chadwick which is incorporated herein by reference. Such operation performs area detection which results in higher sensitivity performance than experienced with linear detection systems. This is because TDI mode permits longer effective exposures than line sensors. Computer 50 controls the mode and operation of the sensor via controller 69. In the TDI mode, the transfer of the charge in the CCD must be matched to the speed of the stage moving the wafer under the module to prevent image blurring.

FIG. 4 illustrates a method of controlling the sensor 68 using the stage's motion for timing and scanning of a wafer in time-delay integration mode. An encoder is attached to the x-stage and its signal is fed into the controller. The computer directs the controller to start the CCD integration of the received signal, and in step 120 the computer also directs the stage to move to the other end of the wafer at a constant velocity. The controller checks the encoder output from the stage to determine whether the stage has moved one pixel's length in step 121. If the stage has moved exactly one pixel, then in step 122 the CCD's charge is transferred down one row and the last row of the CCD is read out in step 123 and transferred to the digitizer 70. This process continues until the stage has reached the other end of the wafer and the scanning stops at step 124. To complete the scanning of the entire wafer's surface, at step 125 the stage returns back to the starting point and is indexed in the y-direction by one module's field of view in step 126. The x-pass starts over with the CCD integration as described above in steps 120–127 until enough scans have occurred to cover the wafer. It should be understood that other scanning procedures can be employed with many types of imaging arrays, not just a CCD array. For example, the array may be a CMOS photodiode array or a CMOS photogate array, although TDI operation of these sensors may require custom designs of the sensor chips.

With reference to FIG. 3, within board 19 the output of sensor 68 is first digitized by a digitizer 70 to put the signal information into a form with which an image-processor can work. Image-processing to find defects takes place in a detection block 71 where a digital stream is passed to an array of one or more general purpose digital signal processors (DSPs) which implement computer-vision algorithms that recognize and distinguish valid pattern scattering from defect scattering. An advantage of using general purpose DSPs is that algorithms may be changed and tailored to the needs of the user. Alternative computer architectures, such as pipelines or systolic arrays or parallel microprocessors can be used.

Figure 10:
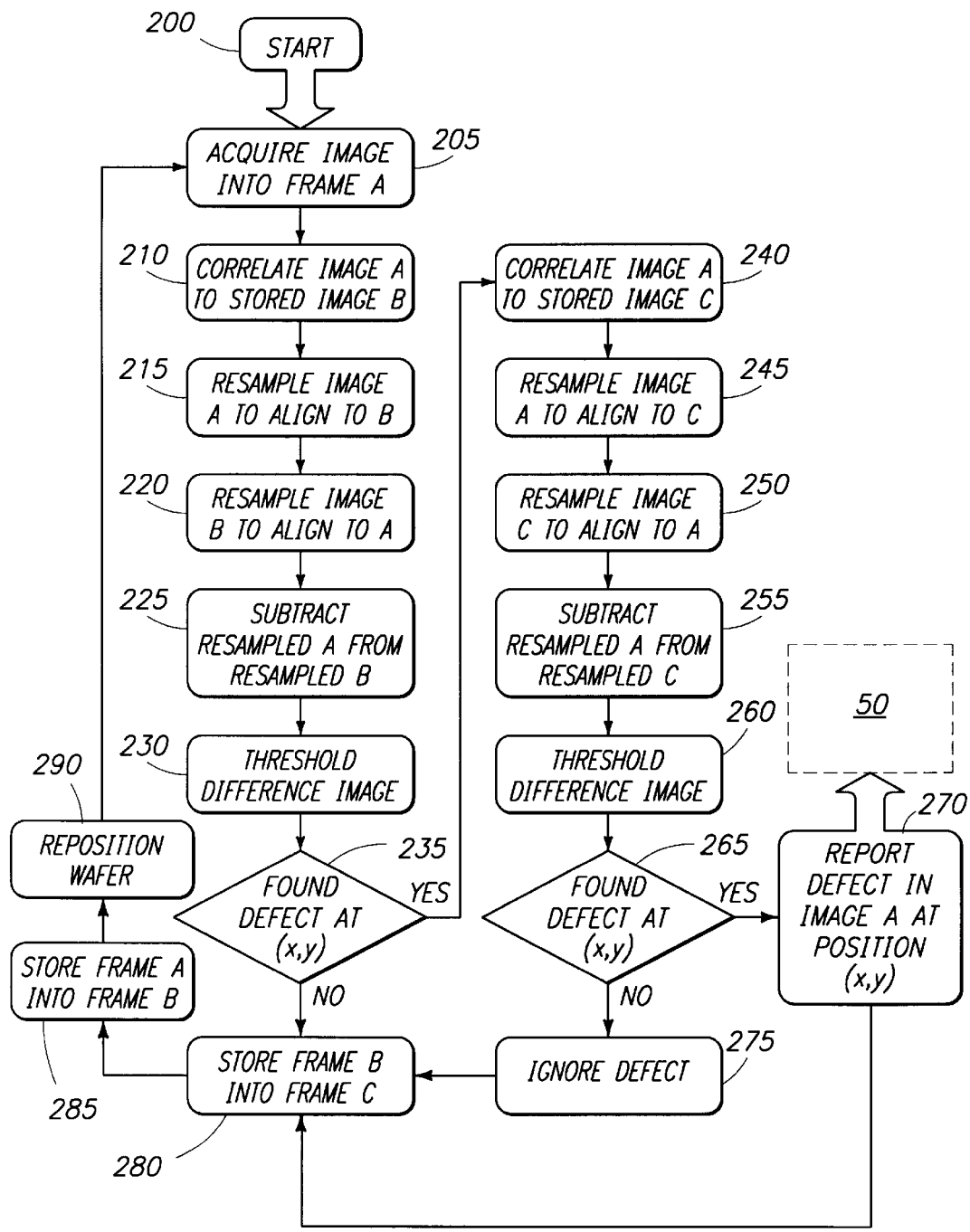
FIG. 10 is a process flow chart describing a die-to-die comparison procedure that may be employed with some embodiments of this invention.

FIG. 10 describes the comparison of images collected using the present invention. This method can be utilized with either brightfield or darkfield inspection and should be performed after Fourier filtering as described above. A common way of separating defect scattering from valid structure scattering is through die-to-die, reticle-to-reticle, or, cell-to-cell comparison of a first stored image and a second image of the corresponding area on the same wafer. A defect is extremely unlikely to appear on corresponding spots of the two dies, so features present on both are considered part of a valid structure. Features present on only one of the dies would be considered defects. To determine which die contains a defect, if a difference is seen in only one die, requires three dies for the comparison. Again, it is extremely unlikely that the defect will be present in exactly the same location on two dies, so a comparison with a third will separate which die contains the defect.

In FIG. 10, this comparison is accomplished after starting at 200, and initially acquiring an image A of the currently inspected portion of the wafer in a step 205. In a step 210, this image A is then correlated to stored image B of a previously inspected corresponding area on the same wafer. Image A is then re-sampled and aligned to image B in a step 215. The results of a correlation of image A to image B indicate the amount of error in aligning the two images opto-mechanically by the system. To subtract the images, they need to be brought into registration with each other. If only one image is re-sampled and moved to be in registration with the second, then the re-sampled image tends to have added noise, while the un-sampled image is sharp. To better keep the eventual processing of the images the same, the procedure is to re-sample each of the two images to half the registration difference between them so that each has been degraded by the re-sampling process the same amount. See step 220. Thus, each image is re-sampled as shown in the flow diagram in FIG. 10. Then in a step 225 the re-sampled image A is subtracted from image B, and a difference between the images is compared against a threshold in a step 230. Next, at a step 235, the system determines if there is defect based upon whether the image subtraction difference was greater than a specified threshold. If it is determined in step 235 that there is a defect on either image A or image B, then, at a step 240, image A is correlated to stored image C of a second previously inspected corresponding area on the same wafer. Image A is then re-sampled and aligned to image C twice, in steps 245 and 250 as described above with reference to steps 215 and 220. Next, re-sampled image A is subtracted from image C and the difference is compared against a threshold as indicated in steps 255 and 260 respectively. If image A is determined to include a defect in step 265, such defect is reported in step 270 for the currently inspected location to main computer 50. Main computer 50 accumulates such defect reports into an aggregate defect database which may be used for various determinations and for implementing any necessary man-machine interfaces. For example, in one embodiment, the invention can be applied to statistical process control of machinery used to manufacture semiconductor wafers using the database to determine when the equipment in question is causing statistically significant numbers of defects.

If no defect is found between images A and C in step 265, the defect found between images A and B in step 235 is ignored in a step 275. In such a case, or if no defect was found in step 235, step 280 stores image B in the frame of image C and step 285 stores image A in the frame of image B. To continue inspection, the wafer is repositioned to the next inspection location in step 290 and the process is repeated beginning at step 205.

In an alternative embodiment, one or more of the imaging subsystems 30 can be replaced with other types of sensors used to detect or measure other wafer processing parameters. For example, sensors can be included which detect other types of defects such as hot spots, or physical parameters such as deposition thickness (as determined by an ellipsometer for example). In one configuration of such an embodiment, a second type of sensor would be located between each imaging subsystem 30. Thus, when the system is used to scan a wafer in the above described manner, in a single pass every other swath is scanned for defects by the imaging subsystem 30, and the alternating swaths are scanned for the second type of characteristic. When the wafer is indexed by the field of view of one module, and the wafer scanned, the swaths previously scanned by one module type are then scanned by the other. By continuing to index across the wafer for additional scans until the entire wafer has been scanned by both types of modules, the wafer is tested for two types of characteristics by one machine in a single inspection. In other embodiments three or more types of modules can be interleaved in parallel to accomplish testing the wafer for three or more characteristics in the same inspection.

Other types of sensor might include various types of optical detector to measure critical dimensions on wafers, brightfield microscopes, etc. In a particularly preferred embodiment, only a single alternative type of detector is provided among the modules and it is positioned at the end of the group of modules. This way, it will interfere minimally with indexing during the scans for wafer defects.

A system, such as shown in FIG. 1, may be interfaced with a robotic wafer loader (not shown) that loads, unloads, and aligns the wafers as required for inspection. In uses such as statistical process control of wafer manufacturing machinery, wafers are tested as fast and as often as possible to detect when a piece of manufacturing equipment is beginning to fail. In a preferred embodiment, the system of this invention is small enough to integrate with existing equipment so that in-situ or integrated inspections may be performed before the wafer exits the processing tool.

In one embodiment, the system 10 shown in FIG. 1 is incorporated with a multi-step processing tool such as a "cluster tool" or a "phototrack" tool. In such a configuration, the inspection system is used to test the wafers at one or more points between individual processes performed within the batch tool. In the case of a cluster tool, the inspection system may be mounted on one of the major or minor facets of the tool. Cluster tools are known in the art and are available from Applied Materials of Santa Clara, Calif. and Novellus Systems, Inc. of San Jose, Calif. for example.

Figure 11:
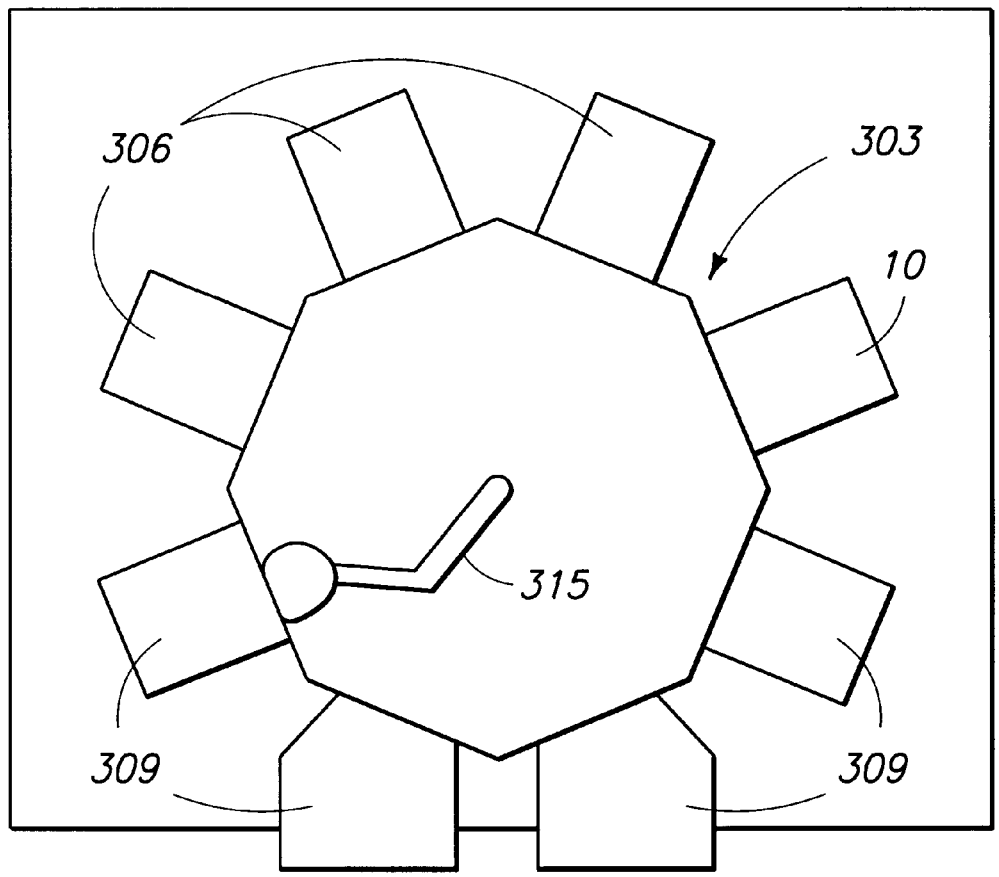
FIG. 11 is a schematic diagram of a cluster tool incorporating the modular inspection system of the present invention.

A cluster tool, such as that depicted in FIG. 11, employs a central wafer handling "polygon" 303 with small single-wafer process tools 306 and ancillary function tools 309 mounted to the outer "facets" of polygon 303 in sequence. Examples of process tools 306 include CVD reactors, etchers, and strippers while ancillary function tools 309 may perform, for example, cassette load-lock, wafer alignment, de-gas, or cool-down. Each of these tools 306 and 309 are accessible to a central handling robot 315 which delivers wafers to these tools in succession. Typically, the entire system operates at constant vacuum. In one embodiment, the inspection system is integrated with the cluster tool such that it can perform inspection of a wafer while the wafer is within the cluster tool. In a preferred embodiment depicted in FIG. 11, the inspection system 10 is mounted to one of the outer facets of polygon 303 (either a primary or secondary cluster port) and is also accessible to central handling robot 315 for delivery of the wafers to the inspection system 10. The inspection system can alternatively be incorporated within the polygon 303 and accessible to central handling robot 315, thus not utilizing an outer facet of the polygon. Preferably, inspection system 10 facilitates monitoring of the performance of one or more of process tools 306.

Because it may, in some cases, be difficult to integrate an inspection tool of this invention in the interior of a third-party cluster tool or phototrack tool, a preferred embodiment of this invention provides an inspection tool on the exterior of a batch tool. In this case, the inspection tool need not be introduced into the vacuum environment of the tool's interior. Rather it can be mounted on a window of one of the major or minor facets of the cluster tool for example. In a particularly preferred embodiment, the inspection tool is mounted on the window of a cool-down chamber. In operation, the wafer in the cool-down chamber is raised to a point near the window. The inspection tool then images the wafer by directing a light beam through the window and onto the wafer in the chamber. The light scattered or reflected from the wafer passes back through the window to the inspection tool where it is monitored by a detector. The optics of the inspection tool may have to be modified to account for the reflection and refraction from the window.

The current invention realizes several advantages over prior conventional systems. One advantage of the current invention is that it allows high-speed inspection of semiconductor wafers. This is accomplished by stacking multiple inspection modules side-by-side within the inspection system 10 as shown in FIG. 1, and using them in parallel to cover multiple regions on a wafer simultaneously. Miniaturized illumination, optics, and sensor components makes this possible by allowing the modules themselves to be compact and very thin, preferably less than about 50 mm, and more preferably between 20 and 40 mm. In one specific embodiment, the modules are approximately 22 mm thick. The Fourier filter system of the present invention, which permits using a single motor to accomplish Fourier filtering, further facilitates the low profile of the modules. The use of parallel sensor modules and TDI operation allows sufficient exposures for each pixel to be easily achieved while maintaining adequate overall inspection speed. Also, being stacked in parallel, the field of view of each module can be kept small. This allows the use of low-cost laser diodes and relaxed-requirement optical lenses used to image, resulting in significant cost savings. Further, relaxed sensitivity requirements allow the use of commercial grade CCD sensors which also reduces costs.

In addition, because of the small size and speed of the system, it can be incorporated with manufacturing tools such that wafers can be inspected at various points in the manufacturing process, thus decreasing time to detection and therefor decreasing any time lost in further processing defective wafers. This advantage is realized in both batch processing and cluster tool processing. Another advantage provided by the size and speed of the inspection system of the current invention is, that when incorporated with manufacturing tools for statistical process control, it can more quickly detect tool failures and thus reduce the losses due to wafer defects caused by that tool before its failure was detected with the current inspection systems.

Additionally, use of TDI to facilitate area detection, as well as the variability of illumination angle, azimuth, and polarization provide increased sensitivity over systems that use linear detection. Also, the use of fully collimated illumination increases the light collection efficiency of the system.

Other embodiments and advantages will be apparent to those skilled in the art from consideration of the specification and practice of the invention disclosed herein. It is intended that the specification and examples be considered as exemplary only, with a true scope of the invention being indicated by the following claims.

What is claimed is:

1. An integrated circuit manufacturing system comprising:
    (a) a plurality of interrelated integrated circuit manufacturing tools capable of operating in parallel on a plurality of semiconductor wafers;
    (b) a modular optical inspection system including
        a plurality of modular inspection subsystems each configured to detect defects on a portion of a semiconductor wafer;
        a mechanism for moving at least one of the semiconductor wafer and the plurality of modular inspection subsystems with respect to one another;
        a Fourier filter system comprising:
            a continuous translatable medium having transparent regions and opaque regions in fixed spatial relation to one another and defining multiple Fourier filters: and
            a translation mechanism arranged to translate said translatable medium such that individual Fourier filters are presented for filtering light;
    wherein the modular optical inspection system is disposed above a window of a cooling stage of one of the plurality of integrated circuit manufacturing tools; and
    (c) a handling tool for moving the semiconductor wafers among the plurality of manufacturing tools and the inspection system.

2. The integrated circuit manufacturing system of claim 1, wherein the plurality of interrelated integrated circuit manufacturing tools comprise a cluster tool.

3. The integrated circuit manufacturing system of claim 1, wherein each of the modular inspection subsystems has a field of view spanning a fraction of the width of the semiconductor wafer.

4. In an integrated circuit manufacturing system including a plurality of interrelated integrated circuit manufacturing tools capable of operating in parallel on a plurality of semiconductor wafers, a method of inspecting a semiconductor comprising:
    transferring the semiconductor wafer from one of the plurality of manufacturing tools to a modular optical inspection system including
        a plurality of modular inspection subsystems each configured to detect defects on a portion of the semiconductor wafer wherein the modular optical inspection system is disposed above a window of a cooling stage of one of the plurality of integrated circuit manufacturing tools; and
        a Fourier filter system comprising:
            a continuous translatable medium having transparent regions and opaque regions in fixed spatial relation to one another and defining multiple Fourier filters; and
            a translation mechanism arranged to translate said translatable medium such that individual Fourier filters are presented for filtering light; and
        moving at least one of the semiconductor wafer and the plurality of modular inspection subsystems with respect to one another such that each of the modular inspection subsystems inspects, in a single pass across the semiconductor wafer, an associated region of the semiconductor wafer.

5. The method of claim 4, wherein the plurality of interrelated integrated circuit manufacturing tools comprise a cluster tool.

6. A modular optical inspection system for inspecting a surface, the inspection system comprising:
    a plurality of modular inspection subsystems each configured to detect defects on a portion of the surface;
    a Fourier filter system comprising:
        a continuous translatable medium having transparent regions and opaque regions in fixed spatial relation to one another and defining multiple Fourier filters; and
        a translation mechanism arranged to translate said translatable medium such that individual Fourier filters are presented for filtering light; and
    a mechanism for moving at least one of the surface and the plurality of modular inspection subsystems with respect to one another, wherein at least one of the plurality of modular inspection subsystems includes
        (i) a two-dimensional sensor configured to receive light from the surface; and
        (ii) a controller configured to control the relative speeds at which data is read from the sensor and the modular inspection subsystem and the surface are moved with respect to one another
    such that the surface is imaged in a time-delay integration mode.

7. The modular optical inspection system of claim 6, wherein all of the plurality of modular inspection subsystems include separate sensors and separate controllers.

8. The modular optical inspection system of claim 6, wherein each of the modular inspection subsystems has a field of view spanning a fraction of the width of the surface.

9. The modular optical inspection system of claim 6, wherein the controller causes one row of pixel data to be read from the two-dimensional sensor each time the at least one inspection subsystem moves by one pixel length with respect to the surface.

10. The modular optical inspection system of claim 6, wherein the two-dimensional sensor includes at least one of a CCD array.

11. The modular optical inspection system of claim 6, wherein at least one of the modular inspection subsystems comprises an illuminator capable of emitting light at a wavelength of no greater than about 500 nm.

12. The modular optical inspection system of claim 6, wherein at least one of the modular inspection subsystems comprises a coherent light source selected from the group consisting of diode lasers, Helium Neon lasers, Argon lasers, and frequency doubled YAG lasers.

13. The modular optical inspection system of claim 6, wherein at least one of said modular inspection subsystems contains an ellipsometer configured to measure the thickness of a layer on the surface.

14. A modular optical inspection system for inspecting a surface, the inspection system comprising:
    a plurality of modular inspection subsystems each configured to detect defects on a portion of the surface;
    a mechanism for moving at least one of the surface and the plurality of modular inspection subsystems with respect to one another;
    a Fourier filter system comprising:
        a continuous translatable medium having transparent regions and opaque regions in fixed spatial relation to one another and defining multiple Fourier filters; and
        a translation mechanism arranged to translate said translatable medium such that individual Fourier filters are presented for filtering light; and
    a master processor configured to process data delivered from at least some of the modular inspection subsystems,
    wherein a first one of the plurality of modular inspection subsystems includes a local processor configured to process data collected by the first modular inspection subsystem.

15. The modular optical inspection system of claim 14, wherein all of the plurality of modular inspection subsystems include separate local processors.

16. The modular optical inspection system of claim 15, wherein the master processor is connected to each of the separate local processors.

17. The modular optical inspection system of claim 14, wherein each of the modular inspection subsystems has a field of view spanning a fraction of the width of the surface.

18. The modular optical inspection system of claim 14, wherein the local processor comprises a digital signal processor.

19. The modular optical inspection system of claim 14, wherein local processor implements an algorithm that distinguishes valid pattern scattering from defect scattering on the surface.

20. A Fourier filter system for use in a surface inspection system, the Fourier filter system comprising:
    a continuous translatable medium having transparent regions and opaque regions in fixed spatial relation to one another and defining multiple Fourier filters; and
    a translation mechanism arranged to translate said translatable medium such that individual Fourier filters are presented for filtering light.

21. The Fourier filter system of claim 20, wherein spacing between the opaque regions varies substantially continuously over at least a segment of the translatable medium defining at least two Fourier filters.

22. The Fourier filter system of claim 20, wherein at least a segment of the translatable medium is divided into discrete Fourier filters.

23. The Fourier filter system of claim 20, wherein the translatable medium contains an etched metal.

24. The Fourier system of claim 20, wherein the translatable medium contains a transparent medium on which said opaque regions reside.

25. The Fourier filter system of claim 20, wherein the translatable medium includes parallel strips defining said opaque regions.

26. The Fourier filter system of claim 20, wherein the opaque regions comprise discrete spots.

27. The Fourier filter system of claim 20, wherein the translation mechanism comprises an actuator.

28. The Fourier filter system of claim 27, wherein the translation mechanism further comprises a roller which rotates under torque from the actuator, thereby translating said translatable medium.

29. The Fourier filter system of claim 27, wherein the translation mechanism has a single actuator only.

30. The Fourier filter system of claim 20, wherein the translation mechanism comprises a mechanism arranged to engage an actuator.

31. The Fourier filter system of claim 20, wherein the translatable medium comprises a closed loop.

32. A modular optical inspection system for inspecting a surface having known valid feature patterns defining functional aspects of the surface, the inspection system comprising:
    a plurality of modular inspection subsystems each configured to detect defects on a portion of the surface; and
    a mechanism for moving at least one of the surface and the plurality of modular inspection subsystems with respect to one another, wherein at least one of the plurality of modular inspection subsystems includes
        (i) a continuous translatable medium having transparent regions and opaque regions in fixed spatial relation to one another and defining multiple Fourier filters; and
        (ii) a translation mechanism arranged to translate said translatable medium such that individual Fourier filters are presented for filtering light.

33. The modular optical inspection system of claim 32, wherein spacing between the opaque regions varies substantially continuously over at least a segment of the translatable medium defining at least two Fourier filters.

34. The modular optical inspection system of claim 32, wherein at least a segment of the translatable medium is divided into discrete Fourier filters.

35. The modular optical inspection system of claim 32, wherein the translation mechanism comprises a single actuator.

36. In a surface inspection system having a Fourier filter sub-system defining multiple Fourier filters, a method of filtering an image of a surface, the method comprising:
    (a) selecting a Fourier filter from the Fourier filter sub-system by
        (i) illuminating a region of the surface containing valid features;
        (ii) passing an opaque region or aperature through a Fourier image plane of the illuminated region of the surface and monitoring changes in light intensity passing through the filter;

(iii) determining a spatial frequency of a light intensity distribution in the Fourier image plane, the light intensity distribution being associated with valid periodic surface features; and (iv) identifying a selected Fourier filter having a spatial frequency matching that of the light intensity distribution; and (b) positioning said selected Fourier filter in the Fourier image plane;

wherein the Fourier filter sub-system comprises a continuous translatable medium in including transparent regions and opaque regions of fixed spatial relation to one another and defining the multiple Fourier filters.

37. The method of claim 36 further comprising:

in (a), determining a phase or position of the light intensity distribution; and in (b), aligning the selected Fourier filter in the Fourier image plane to match the phase or position of the light intensity distribution.

38. The method of claim 36, wherein the opaque region is a strip of opaque material spanning substantially the length of the Fourier image plane.

* * * * *